(12) United States Patent
Sakai et al.

(10) Patent No.: US 7,727,212 B2
(45) Date of Patent: Jun. 1, 2010

(54) ABSORBENT ARTICLE FOR SANITARY NAPKIN

(75) Inventors: Akane Sakai, Kanonji (JP); Wataru Yoshimasa, Kanonji (JP); Kazuya Nishitani, Kanonji (JP); Satoshi Mizutani, Kanonji (JP)

(73) Assignee: Uni-Charm Corporation, Kawanoe-shi (JP)

( * ) Notice: Subject to any disclaimer, the term of this patent is extended or adjusted under 35 U.S.C. 154(b) by 334 days.

(21) Appl. No.: 11/423,567

(22) Filed: Jun. 12, 2006

(65) Prior Publication Data

US 2006/0287636 A1  Dec. 21, 2006

(30) Foreign Application Priority Data

Jun. 17, 2005 (JP) ............................. 2005-178567

(51) Int. Cl.
*A61F 13/15* (2006.01)
*A61F 13/20* (2006.01)

(52) U.S. Cl. ............................... 604/385.201; 604/383; 604/385.31; 604/366

(58) Field of Classification Search ................ 604/366, 604/385.31, 385.201, 383
See application file for complete search history.

(56) References Cited

U.S. PATENT DOCUMENTS

| | | | | |
|---|---|---|---|---|
| 3,639,199 A | * | 2/1972 | Brandts et al. ............... 428/110 |
| 4,886,513 A | * | 12/1989 | Mason et al. ........... 604/385.31 |
| 5,360,421 A | * | 11/1994 | Revelle ....................... 604/378 |
| 5,514,104 A | * | 5/1996 | Cole et al. ................... 604/366 |
| 5,545,156 A | * | 8/1996 | DiPalma et al. ........ 604/385.23 |
| 5,578,025 A | * | 11/1996 | May ....................... 604/385.31 |
| 5,624,423 A | * | 4/1997 | Anjur et al. ............ 604/385.21 |
| 5,688,259 A | * | 11/1997 | Osborn et al. .......... 604/385.01 |
| 5,795,345 A | * | 8/1998 | Mizutani et al. ............. 604/380 |
| 6,171,291 B1 | * | 1/2001 | Osborn et al. .......... 604/385.23 |
| 6,217,563 B1 | * | 4/2001 | Van Gompel et al. . 604/385.101 |
| 6,284,943 B1 | * | 9/2001 | Osborn et al. ............... 604/366 |
| 6,326,525 B1 | * | 12/2001 | Hamajima et al. .......... 604/378 |
| 6,423,043 B1 | * | 7/2002 | Gustafsson ............ 604/385.01 |
| 6,425,889 B1 | * | 7/2002 | Kitaoka et al. ......... 604/385.01 |
| 6,685,690 B2 | * | 2/2004 | Ikeda et al. .............. 604/385.3 |

(Continued)

FOREIGN PATENT DOCUMENTS

JP    H11-033054    2/1999

(Continued)

*Primary Examiner*—Tatyana Zalukaeva
*Assistant Examiner*—Susan Su
(74) *Attorney, Agent, or Firm*—Morrison & Foerster LLP

(57) ABSTRACT

An absorbent article worn in the groin area, in which, when a compressive force is received from a lateral direction, a main absorbent region can oppose an excretion area of a wearer's body without twists or wrinkles occurring, and when the compressive force is relaxed, the article easily recovers to its original shape. An absorbent body provided in the absorbent article has a main absorbent region, reinforcing regions, and buffer regions. The bending stiffness of the reinforcing regions and the main absorbent region is larger than that of the buffer regions. When compressive force is received from a wearer's thigh areas in the lateral direction, the reinforcing regions that are positioned to the left and right deform in a curved shape, and the buffer regions that are to the left and right are compressed. The main absorbent region does not easily deform, and maintains a tight fit.

14 Claims, 11 Drawing Sheets

U.S. PATENT DOCUMENTS

| | | | |
|---|---|---|---|
| 7,220,251 B2 * | 5/2007 | Otsubo et al. | 604/385.201 |
| D548,337 S * | 8/2007 | Ueminami | D24/124 |
| 7,312,372 B2 * | 12/2007 | Miyama et al. | 604/380 |
| 2002/0087134 A1 * | 7/2002 | Drevik et al. | 604/378 |
| 2002/0115979 A1 * | 8/2002 | Ikeda et al. | 604/385.101 |
| 2002/0193767 A1 * | 12/2002 | Mavinkurve et al. | 604/385.04 |
| 2003/0050617 A1 * | 3/2003 | Chen et al. | 604/378 |
| 2006/0224138 A1 * | 10/2006 | Heki et al. | 604/385.31 |
| 2006/0276767 A1 * | 12/2006 | Ueminami et al. | 604/385.31 |

FOREIGN PATENT DOCUMENTS

| | | |
|---|---|---|
| JP | 3455232 | 7/2003 |
| JP | 2004-141619 | 5/2004 |
| JP | 2004-154153 | 6/2004 |
| JP | 2004-154154 | 6/2004 |
| JP | 2004-181084 | 7/2004 |
| JP | 2004-229766 | 8/2004 |
| JP | 2004-350908 | 12/2004 |
| JP | 2005-007144 | 1/2005 |
| WO | WO-98/29076 | 7/1998 |

* cited by examiner

ABSORBENT ARTICLE FOR SANITARY NAPKIN

This application claims the benefit of priority from Japanese Patent Application No. 2005-178567, filed on Jun. 17, 2005, the content of which is incorporated herein by reference.

BACKGROUND OF THE INVENTION

1. Field of the Invention

The present invention relates to absorbent articles that are used as sanitary napkins for absorbing menstrual blood, panty liners for absorbing vaginal discharge, urine absorbing pads, or the like, and are worn in the groin area.

2. Related Art

Absorbent articles worn in a female's groin area are used as sanitary napkins for absorbing menstrual blood, panty liners for absorbing vaginal discharge, urine absorbing pads, or the like. When this type of absorbent article is worn in a female's groin area, force acts from the left and right thigh areas to compress the absorbent article in a lateral direction. By this force, the absorbent article easily bends along a centerline in a longitudinal direction, or a central region deforms into a convex shape towards a wearer's body, or the central region deforms into a concave shape tending to separate from the body. Furthermore, by the absorbent article being sandwiched by the left and right thigh areas, the width dimension of an absorbent body is reduced, the compressive force extends towards the front and the rear of the absorbent body, and the width of the overall absorbent body is narrowed. When the absorbent article deforms in this way, a gap is easily formed between the absorbent body and the excretion area of the wearer's body, and there is a risk that menstrual blood, urine, or the like may leak in a lateral direction or to the rear of the absorbent article.

Furthermore, in states in which the absorbent article is attached to underwear, and also when removed together with underwear after being used for a prescribed length of time, the absorbent article easily remains deformed in a convex or a concave shape, or the width dimension remains narrowed. As a result, the absorbent body cannot recover to its original shape, and a user can easily be made apprehensive as to whether menstrual blood or urine is leaking from the absorbent article.

For example, as described in Japanese Patent Application, Laid Open No. H11-33054, an absorbent article is known in which a compressed line, compressed in a concave shape, is formed in an absorbent body, and a central absorbent area is enclosed by this compressed line. When this absorbent article is worn in the groin area, pressure from the thigh areas is concentrated on and acts on the compressed line, the central absorbent area enclosed by the compressed line deforms into a convex shape towards a wearer's body and easily makes contact with the wearer's body, and when the compressive force is released, the compressed line exhibits an elastic restorative capability so that it can be anticipated that the absorbent area will recover to a wide state. However, when excreted fluid is absorbed, since the compressive force of the compressed line weakens and the elastic capability decreases, after the compressive force from the thigh areas is released, the central area cannot recover to a wide state, and a state with the width dimension narrowed is easily maintained. As a result, the absorbent article during use cannot widely cover the wearer's body, leakage of menstrual blood and the like can easily occur, and since the width dimension is narrowed after usage, the user can easily be made apprehensive as to whether menstrual blood or the like has leaked.

Furthermore, Japanese Patent Application, Laid Open No. 3455232 discloses a sanitary napkin in which a stabilizing member is arranged extending in a lateral direction, at the front end portion and the rear end portion. This stabilizing member can exhibit an elastic force in a lateral direction, and when the sanitary napkin receives a compressive force from the left and right, the stabilizing member that is positioned at the front portion and the rear portion can exhibit a resistance force against the compressive force.

However, although the sanitary napkin disclosed in Japanese Patent Application, Laid Open No. 3455232 can exhibit a resistance force against the compressive force from a lateral direction, at the front end portion and the rear end portion, it cannot exhibit a resistance force against the compressive force from the lateral direction in an intermediate region between the front and rear of the sanitary napkin, and when the sanitary napkin is worn, it is not possible to avoid a large contraction in the lateral direction of the absorbent body at the intermediate region.

SUMMARY OF THE INVENTION

An object of the present invention is the provision of an absorbent article that solves the above-described conventional problems. The present invention has as an object the provision of an absorbent article in which, when the article is worn in the groin area and sandwiched by the thigh areas, and when the article receives a compressive force from a lateral direction, a main absorbing region positioned in the center is affected as little as possible by the compressive force, a tight fit is easily sustained between the main absorption region and an excretion area of a wearer's body, and when pressure from the thigh areas is relaxed, the article easily recovers to its original width dimension.

The present invention is formed of the absorbent article that is worn in the groin area, with a longitudinal direction in a lengthwise orientation and a lateral direction in a direction orthogonal to the longitudinal direction, the article including an absorbent body having a main absorbent region positioned on a centerline in the longitudinal direction, a top sheet that is permeable to fluids, covering a skin-side face of the absorbent body, a back sheet covering a garment-side face of the absorbent body, buffer regions with stiffness lower than the main absorbent region, positioned to the left and right sides of the main absorbent region, and side portion reinforcing regions with stiffness larger than the buffer regions, positioned at left and right external sides of the buffer regions and extending in the longitudinal direction.

When the absorbent article of the present invention, in a state when worn in the groin area, receives compressive force in a lateral direction from the thigh areas, the side portion reinforcing regions positioned at the left and right sides exhibit an elastic force and deform easily so as to flex towards a centerline in a longitudinal direction. By this deformation of the side portion reinforcing regions, the buffer regions that are soft and are positioned on the inside thereof are compressed and deformed; however, since the stiffness of the main absorbent region is higher than that of the buffer regions, even if the buffer regions are compressed, the compressive force is not easily transmitted to the main absorbent region. As a result, extreme compression deformation of the main absorbent region can be curtailed, and in a state in which a relatively wide area is ensured for the main absorbent region, a tight fit to the excretion area of the wearer's body is facilitated.

Preferably, the present invention includes a front reinforcing region and a rear reinforcing region whose bending stiffness in the lateral direction is larger than the buffer regions, connecting, among the side portion reinforcing regions, a left side portion reinforcing region and a right side portion reinforcing region, wherein the buffer regions include a front buffer region positioned between the main absorbent region and the front reinforcing region, and a rear buffer region positioned between the main absorbent region and the rear buffer region.

With the front reinforcing region and the rear reinforcing region provided, the side portion reinforcing regions positioned at the left and right sides are supported at the front and rear by the front reinforcing region and the rear reinforcing region, and when compressive force is received from the thigh areas, in the side portion reinforcing regions, an intermediate region in the longitudinal direction easily bends into a convex shape towards a longitudinal direction centerline. As a result, the buffer regions on the two sides of the main absorbent region compress and deform, and deformation, in which the width dimension of the overall absorbent body contracts, does not easily occur. In addition, when the compressive force from the thigh areas is relaxed, the absorbent article easily returns to its original form.

In the present invention the main absorbent region, the buffer regions, and the side portion reinforcing regions are formed in the absorbent body. Moreover, the main absorbent region, the buffer regions, the side portion reinforcing regions, the front reinforcing region, and the rear reinforcing region are arranged in the absorbent body.

The present invention has absorbent sheets forming the absorbent body, and in the side portion reinforcing regions the absorbent body is folded. Alternatively, in the present invention, the absorbent body has absorbent sheets and an absorbent core, constructed by being laid on one another; the side portion reinforcing regions are formed by both side portions of the absorbent sheets being folded; and the main reinforcing region is a portion that has the absorbent core.

Moreover, in the side portion reinforcing regions of the present invention, the folded absorbent sheets may be fixed together by an adhesive. Furthermore, in the present invention, the weight of the absorbent body may be composed so that the side portion reinforcing regions are larger than the buffer regions, and the main absorbent region is larger than the buffer regions. In such cases, when the absorbent body is compressed in the direction of thickness, the bending stiffness difference between the main reinforcing region, the buffer regions, and the side portion reinforcing regions is easily enlarged.

In addition, in the present invention, the absorbent body is compressed in the direction of thickness. In the main reinforcing region, an upper absorbent core is preferably laid upon the absorbent body. In the main absorbent region, when the upper absorbent core is laid upon the absorbent body, the skin side face of the main absorbent region can be formed in a convex shape, and the main absorbent region is easily tightly fitted to the excretion area of the wearer's body. In addition, the main absorbent region does not deform easily.

For example, in the front reinforcing region and the rear reinforcing region of the present invention, a plurality of absorbent sheets are fixed via an adhesive. In the side portion reinforcing regions of the present invention, the absorbent body is preferably reinforced by a reinforcing sheet that includes thermoplastic resin. If the reinforcing sheet is provided, in a state in which the side portion reinforcing regions have absorbed fluid, the bending stiffness of the side portion reinforcing regions can be prevented from excessively decreasing.

Furthermore, in the present invention, to the rear of the main reinforcing region, an intermediate reinforcing region is arranged, with respect to the side portion reinforcing regions, between the left side portion reinforcing region and the right side portion reinforcing region, and the buffer regions are arranged between the intermediate reinforcing region and the side portion reinforcing regions. When the intermediate reinforcing region is arranged in the rear portion of the absorbent article, even if the compressive force acting in a central portion in the longitudinal direction is transmitted to a rear portion, the rear portion is not easily compressed in a lateral direction. Furthermore, by disposing the side portion reinforcing regions, the buffer regions, and the intermediate reinforcing region, in order, the rear region of the absorbent article easily deforms according to the shape of bulging buttocks.

Furthermore, in the present invention, the side portion reinforcing regions have a discontinuous portion in the rear region, and bending stiffness in the lateral direction is smaller for the discontinuous portion than for the side portion reinforcing regions. If the discontinuous portion is provided, when the front region of the absorbent article is compressed and deforms due to compressive force from the thigh areas, transmission of this deforming force to the rear region can be curtailed, and in a state with the rear region of the absorbent article widened, a state with a tight fit to the wearer's body can be sustained.

Additionally, in the present invention, the absorbent body and the back sheet may be fixed via an adhesive, the amount of the adhesive applied per unit area for the side portion reinforcing regions may be larger than that of the buffer regions, and the amount of the adhesive applied per unit area for the main absorbent region may be larger than that of the buffer regions. In this configuration, in the side portion reinforcing regions and the main absorbent region, since the degree of adhesion of the back sheet to the absorbent body formed of fiber is high, it is easier to arrange the bending stiffness of both regions higher than the buffer regions.

According to this type of configuration, when the absorbent article of the present invention is worn in the groin area and receives compressive force from the thigh areas, the main absorbent region does not easily deform such that the width dimension (in the lateral direction) reduces, and the main absorbent region is easily fitted tightly to the excretion area of the wearer's body. In addition, when the compressive force from the thigh areas is relaxed, the absorbent article can easily recover to its original width dimension.

DETAILED DESCRIPTION OF THE INVENTION

An absorbent article of the present invention is a sanitary napkin, a panty liner, a urine absorbing pad, or the like, that is worn in a female's groin area; in the embodiments below, however, a sanitary napkin mainly for absorbing menstrual blood is explained as an example.

Figure 1:
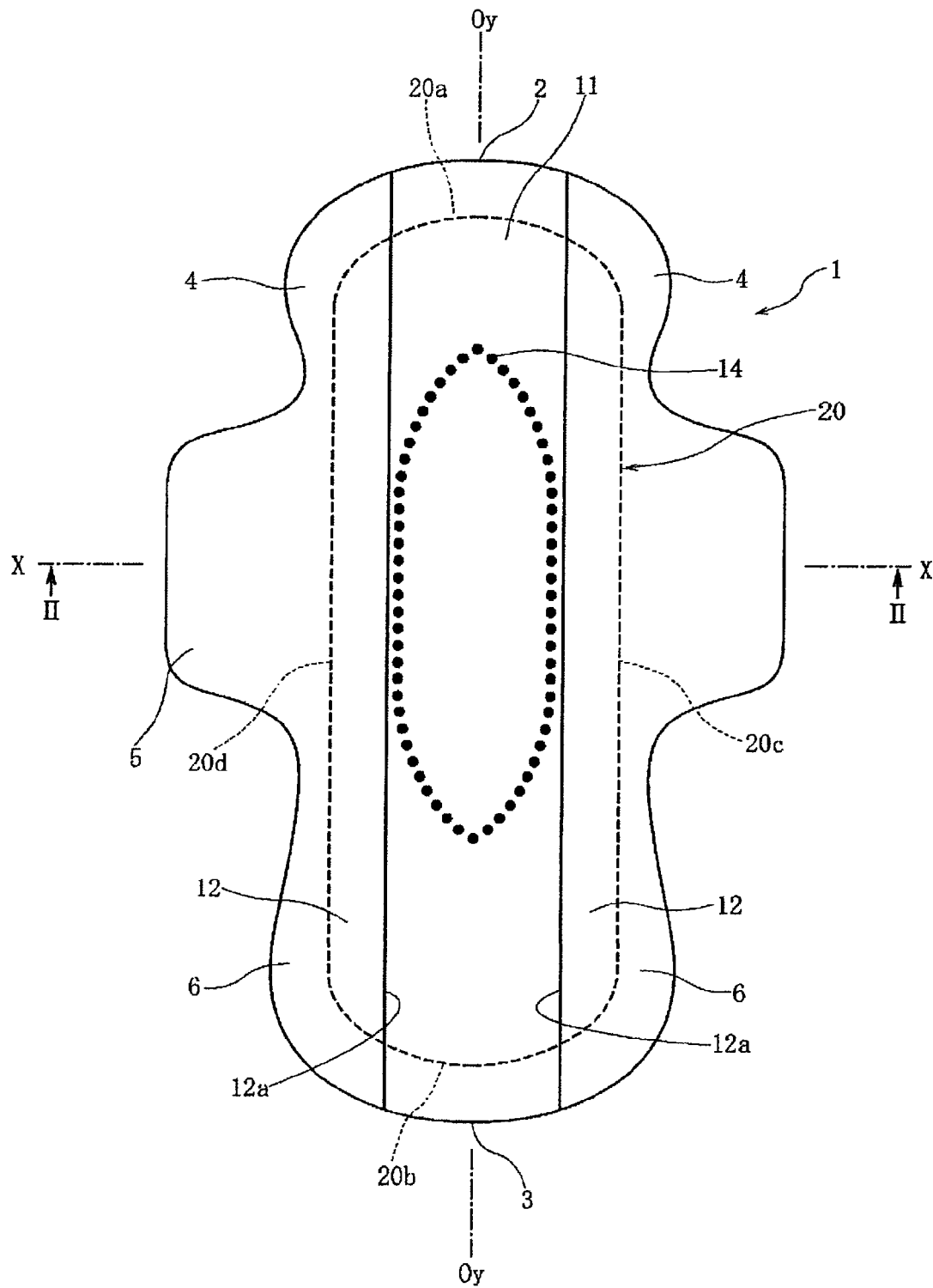
FIG. 1 is a plan view showing a sanitary napkin that is an absorbent article according to a first embodiment.
Figure 2:
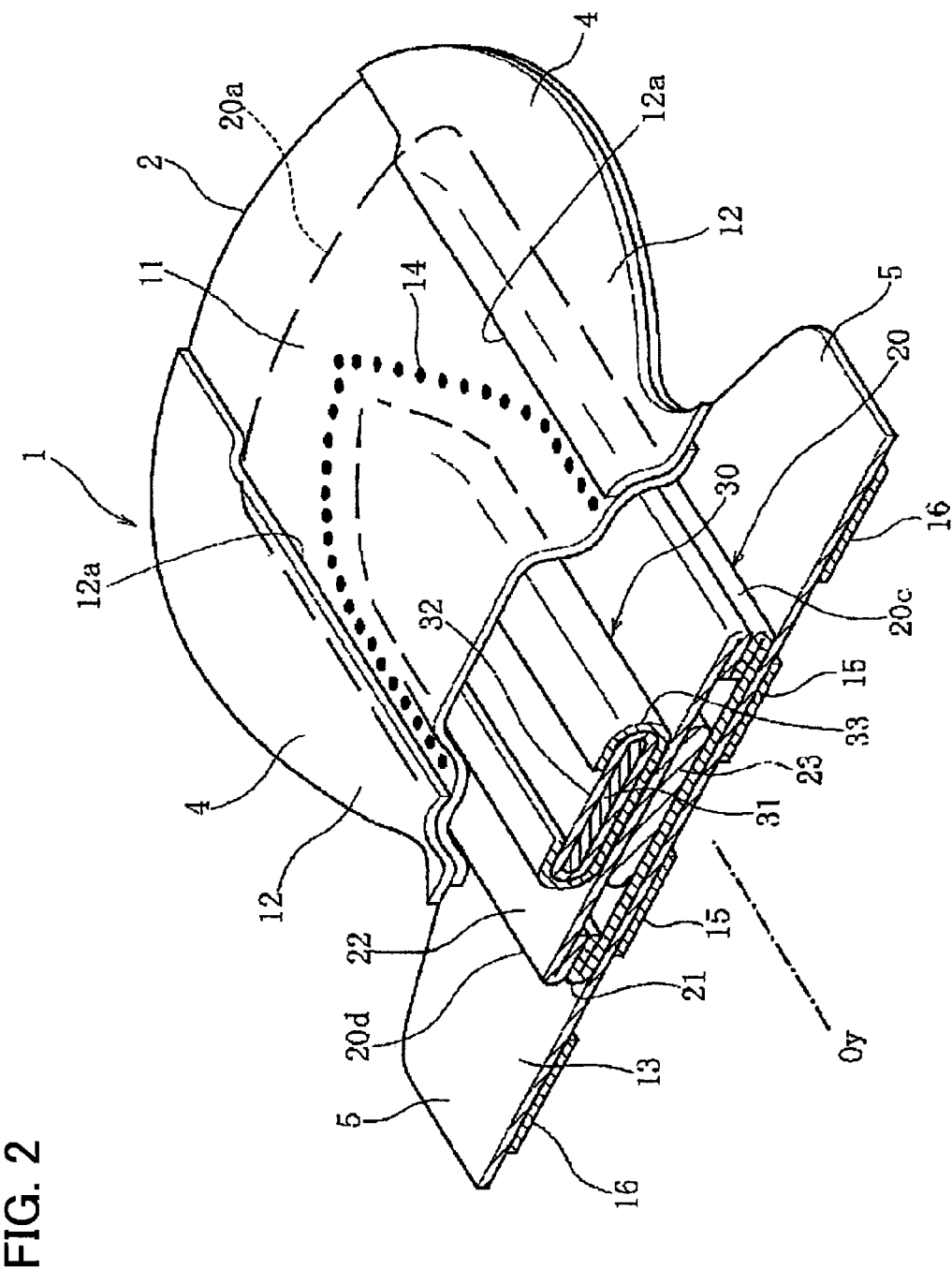
FIG. 2 is a sectional perspective view of the sanitary napkin of FIG. 1, cut along a line II-II.
Figure 3:
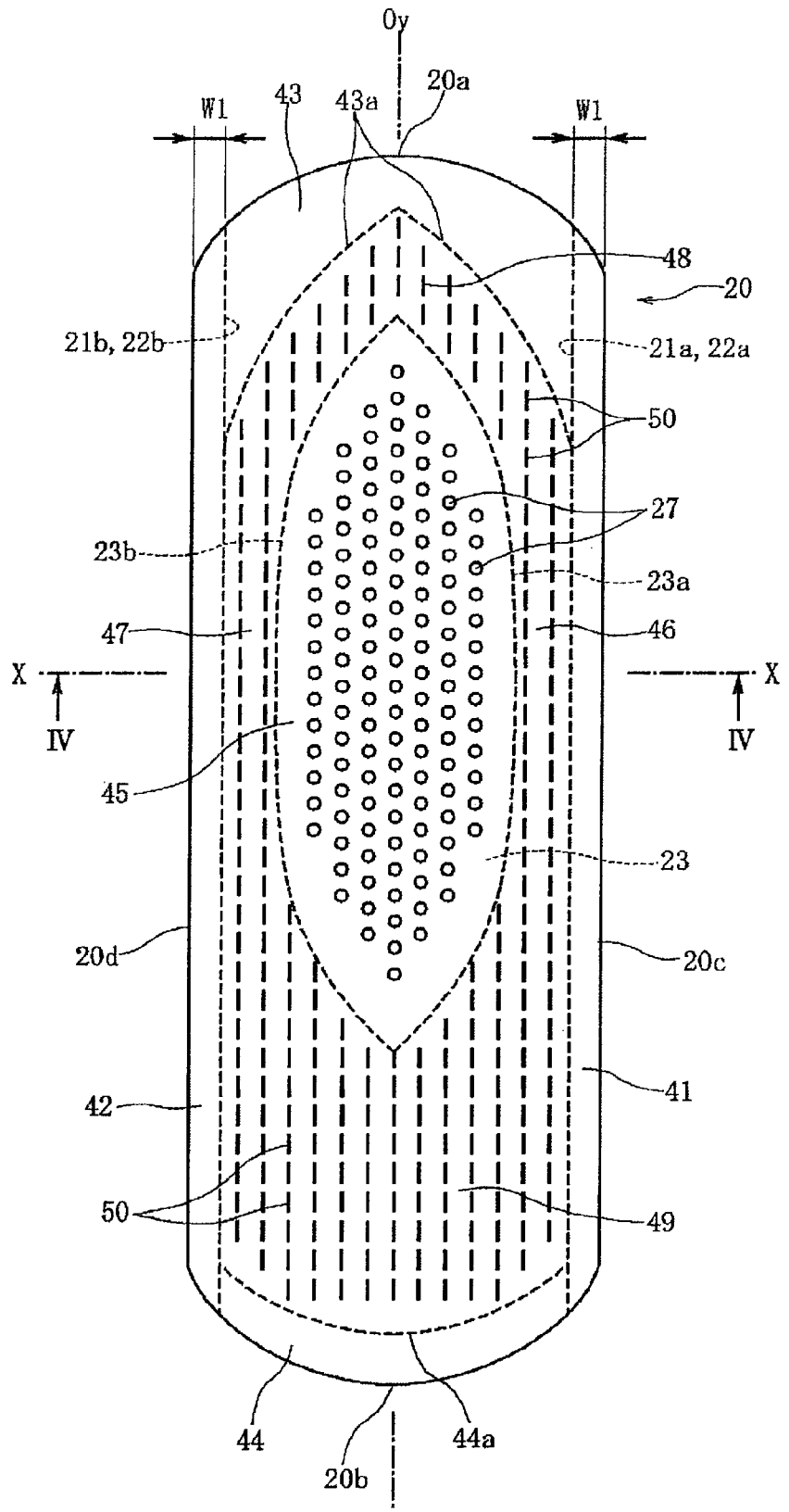
FIG. 3 is a plan view of an absorbent body used in the sanitary napkin.
Figure 4:
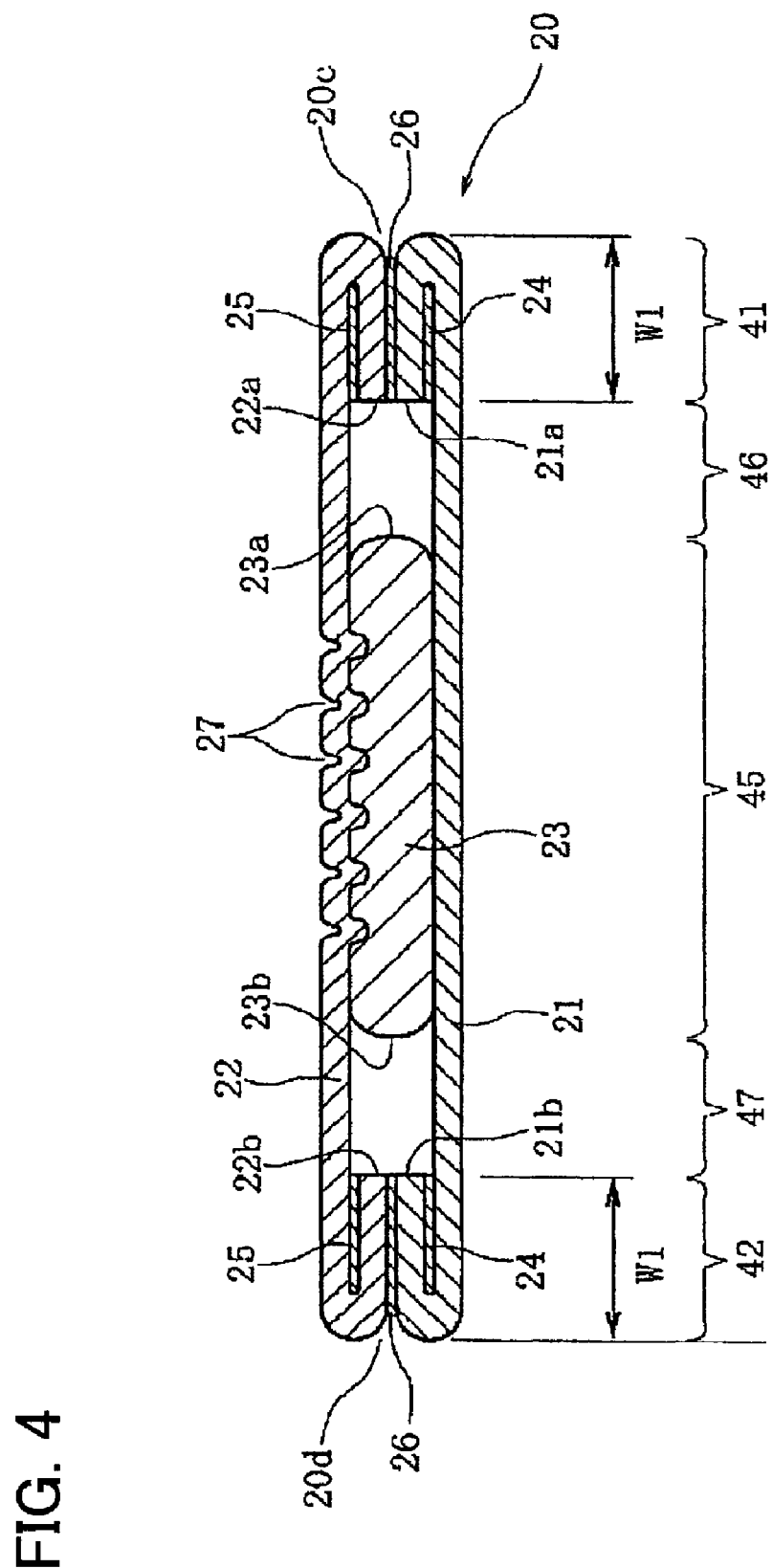
FIG. 4 is sectional view of the absorbent body of FIG. 3, cut along a line IV-IV.
Figure 5:
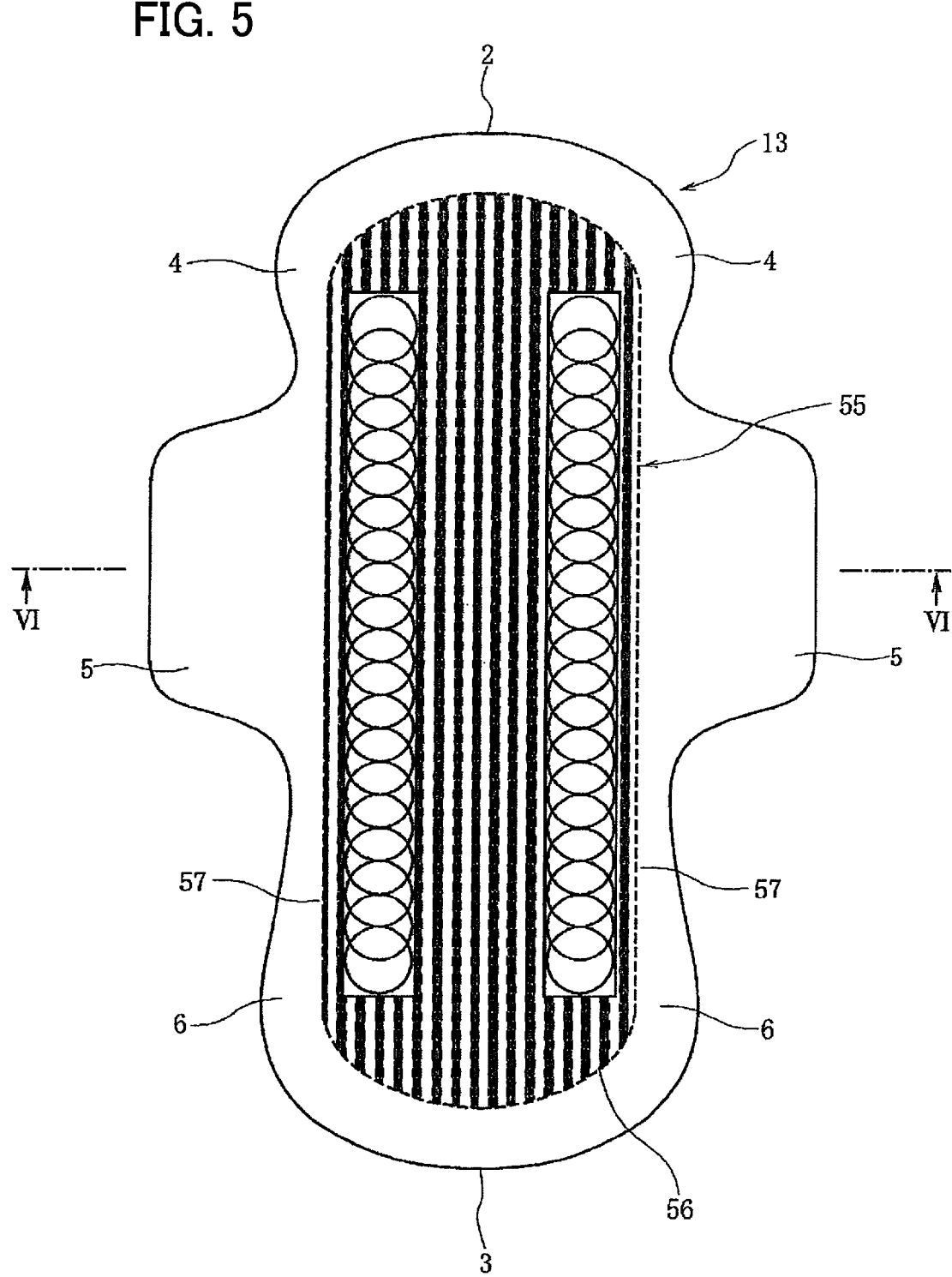
FIG. 5 is a plan view showing an adhesive structure for joining the absorbent body and a back sheet of the sanitary napkin.
Figure 6:
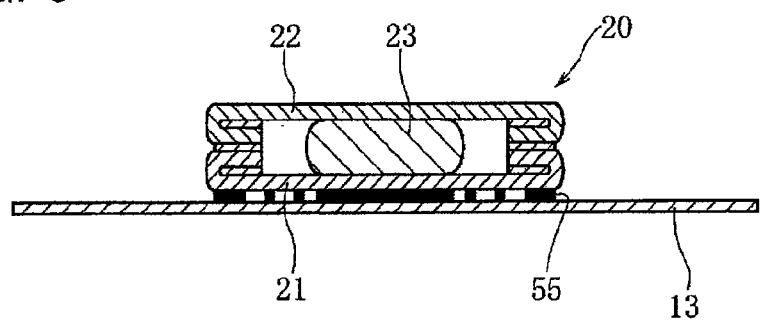
FIG. 6 is a sectional view showing an adhesive structure for joining the absorbent body and the back sheet.

FIG. 1 is a plan view, as seen from a skin-side face, of a sanitary napkin 1 according to a first embodiment of the present invention; FIG. 2 is a sectional perspective view of the sanitary napkin 1 shown in FIG. 1, cut along a line II-II, and with a top sheet and a side sheet partially removed; FIG. 3 is a plan view of an absorbent body arranged in the sanitary napkin 1; FIG. 4 is a diagram for explaining a composition of the absorbent body, and is a sectional view cut along a line IV-IV of FIG. 3; FIG. 5 is a plan view of a back sheet for explaining an amount of an adhesive layer applied for joining the absorbent body and the back sheet of the sanitary napkin 1; and FIG. 6 is a sectional view corresponding to a section along a line VI-VI of FIG. 5, showing a state with the absorbent body and the back sheet joined.

In the following, with regard to the two faces of each element of which the sanitary napkin 1 is composed, a face that faces a wearer's body is referred to as a "skin-side face", and a face on the opposing side is referred to as a "garment-side face". In addition, a lengthwise orientation of the sanitary napkin is referred to as a longitudinal direction, and an orientation orthogonal to the longitudinal direction is referred to as a lateral direction. In so far as dimensions of each element are not particularly specified, a dimension measured in the longitudinal direction is referred to as a length dimension, and a dimension measured in the lateral direction is referred to as a lateral dimension.

As shown in FIG. 1, the sanitary napkin 1 has a front peripheral region 2 with a curved shape and a rear peripheral region 3 with a similar curved shape. The sanitary napkin 1 has an oblong shape with the length dimension at the centerline Oy of the longitudinal direction approximately 150 to 450 mm. The sanitary napkin 1 has both side portions shaped so that, to the front, it has front flap portions 4 and 4 protruding to each of the left and right sides, to the rear of the front flap portions 4 and 4, folded back flap portions 5 and 5 protruding to each of the left and right sides, and farther to the rear of the folded back flap portions 5 and 5, rear flap portions 6 and 6 protruding to each of the left and right sides.

The sanitary napkin 1 has an absorbent body 20. As shown in FIG. 1 and FIG. 3, the absorbent body 20 has a front edge 20a with a curved shape jutting out towards the front, a rear edge 20b with a curved shape jutting out towards the rear, and a right side edge 20c and a left side edge 20d extending in straight lines parallel to the centerline Oy in the longitudinal direction. The front edge 20a of the absorbent body 20 is positioned more towards the inside than the front peripheral region 2 of the sanitary napkin 1, and the rear edge 20b of the absorbent body 20 is positioned more towards the inside than the rear peripheral region 3 of the sanitary napkin 3.

As shown in FIG. 2, an upper absorbent core 30 is arranged on the skin-side face of the absorbent body 20, and a top sheet 11 that is permeable to fluids is placed on the skin-side face of the absorbent body 20 and the upper absorbent core 30. Side sheets 12 and 12 are placed on the skin-side face on both sides of the absorbent body 20. The side sheets 12 are fluid-permeable, but are formed of material with lower fluid permeability than the top sheet 11. A back sheet 13 that is fluid-permeable is placed on the garment-side face of the absorbent body 20.

Between the front edge 20a of the absorbent body 20 and the front periphery region 2 of the sanitary napkin 1, the top sheet 11 and the back sheet 13 are attached by a hot melt type adhesive; between the rear edge 20b of the absorbent body 20 and the rear peripheral region 3 of the sanitary napkin 1, the top sheet 11 and the back sheet 13 are attached by a hot melt type adhesive; and in addition, the top sheet 11 and the back sheet 13 are heat sealed in a prescribed width dimension range towards the inside from each of the front peripheral region 2 and the rear peripheral region 3. At the outer side of the right side edge 20c and at the outer side of the left side edge 20d of the absorbent body 20, the side sheets 12 and the back sheet 13 are attached by a hot melt type adhesive, and the front flap portions 4 and 4, the folded back flap portions 5 and 5, and the rear flap portions 6 and 6 are formed. Furthermore, in the peripheral regions of the front flap portions 4 and 4, the folded back flap portions 5 and 5, and the rear flap portions 6 and 6, the side sheets 12 and the back sheet 13 are heat sealed.

As shown in FIG. 2, the top sheet 11 is placed on both side portions of the skin-side face of the absorbent body 20, and in addition, the side sheets 12 are placed on this skin-side face. The opposing peripheral regions 12a and 12a of the side sheets 12 and 12 are positioned parallel to the centerline Oy in the longitudinal direction, offset at equal distances to the left and right from the centerline Oy in the longitudinal direction. In a region sandwiched by the opposing peripheral regions 12a and 12a, the top sheet 11 and the absorbent body 20 are compressed from the skin side, to form a compressed portion 14. The compressed portion 14 partially pressurizes, with heat applied, the top sheet 11 and the absorbent body 20, and fixes the top sheet 11 and the absorbent body 20 physically or by fusion. The compressed portion 14 is intermittently formed so as to enclose the upper absorbent core 30, and in the region enclosed by the compressed portion 14, the top sheet 11 protrudes together with the upper absorbent core 30 towards the skin-side.

As shown in FIG. 2, on the garment side face of the back sheet 13, pressure sensitive adhesive layers 15 and 15 are provided, extending in a strip in the longitudinal direction on both left and right sides of the centerline Oy in the longitudinal direction. These pressure sensitive adhesive layers 15 and 15 function as fixing devices for fixing the garment side face of the sanitary napkin 1 to an inner face of a crotch portion of underwear. Furthermore, flap portion pressure sensitive adhesive layers 16 and 16 are provided on the garment side face of the back sheet 13, at the folded back flap portions 5 and 5. In a packing state before the sanitary napkin 1 is used, the pressure sensitive adhesive layers 15 and 15 and the flap portion pressure sensitive adhesive layers 16 and 16 are protected by being covered by a separable sheet.

As shown in FIG. 4, the absorbent body 20 has a lower absorbent sheet 21 and an upper absorbent sheet 22, and a lower absorbent core 23 sandwiched between the lower absorbent sheet 21 and the upper absorbent sheet 22.

The lower absorbent sheet 21 and the upper absorbent sheet 22 are formed of hydrophilic material and have a capability of absorbing and retaining fluid, or have inter-fiber voids so as to be able to exhibit a capability of making fluid permeate or diffuse. For example, the lower absorbent sheet 21 and the upper absorbent sheet 22 are formed of air-laid non-woven fabric including pulp fiber, thermoplastic synthetic resin fiber, and a binder of highly absorbent resin (SAP) and an acryl or the like. The air-laid non-woven fabric is made by laminating pulp fiber and synthetic resin fiber, by an air-laid method, to form a fiber weave; highly absorbent resin and binder are included in the fiber weave; pressure is applied between pressurizing rollers; and the fibers are joined by the binder. Alternatively, without including the binder, pressure may be applied between heated rollers, faces of the thermoplastic synthetic resin fiber may be fused, to join the fibers. The thermoplastic synthetic resin fiber is polyethylene (PE) resin fiber, polypropylene (PP) resin fiber, polyethylene telephthalate (PET) fiber, or core-in-sheath composite synthetic fiber with a core of PP resin or PET resin and a sheath of PE resin, or the like.

In this embodiment, the fiber mass of the lower absorbent sheet 21 and the upper absorbent sheet 22 includes 30% to 90% mass of the pulp fiber, 10% to 70% mass of the synthetic resin fiber; in addition the abovementioned highly absorbent resin and acrylic binder are included; and a weight of 100 to 500 g/m$^2$ of air-laid non-woven fabric with a density of 0.03 to 0.2 g/cm$^3$ is used.

For other material of which the lower absorbent sheet 21 and the upper absorbent sheet 22 are composed, non-woven fabric formed of regenerated cellulosic fiber such as rayon fiber or the like, semisynthetic cellulosic fiber such as acetate or the like, thermoplastic synthetic resin fiber, thermoplastic synthetic resin fiber coated with a hydrophilic oil solution, or the like, may be used, and point bond non-woven fabric or through-air non-woven fabric formed by a thermal bonding method, spunlace non-woven fabric formed by a water jet method or a needle punch method, or various other types of material, may also be used. In addition, large weight hydrophilic paper, rayon paper, or layers of these papers, or sheet pulp in which pulp fiber is compressed, or the like, may be used.

For the lower absorbent sheet 21 and the upper absorbent sheet 22, if the synthetic resin fiber is included, the stiffness of the sheets does not deteriorate even in a state with fluid absorbed, and the bending stiffness of the side portion reinforcing regions and the like can be maintained at a high level.

As shown in FIG. 4, the lower absorbent sheet 21 is formed with a right side peripheral portion 21*a* folded back towards the inside, with a folded portion having a width dimension W1, and a left side peripheral portion 21*b* folded back towards the inside, with a folded portion having a width dimension W1. In each of the folded portions, opposing faces of the lower absorbent sheet 21 are fixed by joining with an adhesive 24. In the same way, the upper absorbent sheet 22 is formed with a right side peripheral portion 22*a* folded back towards the inside, with a folded portion having a width dimension W1, and a left side peripheral portion 22*b* folded back towards the inside, with a folded portion having a width dimension W1. In each of the folded portions, opposing faces of the upper absorbent sheet 22 are fixed by joining with an adhesive 25. Furthermore, the folded portion of the lower absorbent sheet 21 and the folded portion of the upper absorbent sheet 22 are fixed by joining with an adhesive 26 in the range of the width dimension W1.

The adhesive 24, 25, and 26 is formed of a hot melt type pressure sensitive adhesive layer, formed, for example, of a plasticizer and an adhesive agent, such as a block copolymer of styrene isoprene styrene (SIS), a block copolymer of styrene butadiene styrene (SBS), a block copolymer of styrene ethylene butadiene styrene (SEBS), a block copolymer of styrene ethylene propylene styrene (SEPS), or the like. Since a large coating amount of the pressure sensitive adhesive can be applied per unit area, the stiffness of the portions joined by the adhesive 24, 25, and 26, can be increased.

As shown in FIG. 3, the folded back portions of the lower absorbent sheet 21 and the upper absorbent sheet 22 extend with the uniform width dimension W1 in the longitudinal direction for the whole length in the longitudinal direction; in the absorbent body 20, a portion formed of the right side folded back portion is the right side portion reinforcing region 41, and a portion formed of the left side folded back portion is the left side portion reinforcing region 42. The width dimension is approximately 3 to 15 mm.

A front reinforcing region 43 is formed at the front portion of the absorbent body 20. The front reinforcing region 43 is formed between the front edge 20*a* of the absorbent body 20 and a border portion 43*a*. A rear reinforcing region 44 is formed at the rear portion of the absorbent body. The rear reinforcing region 44 is formed between the rear edge 20*b* of the absorbent body 20 and a border portion 44*a*.

The front reinforcing region 43 and the rear reinforcing region 44 can be formed by partially making the weight of the fiber of at least one of the lower absorbent sheet 21 and the upper absorbent sheet 22 large; however, in this embodiment, the front reinforcing region 43 and the rear reinforcing region 44 are formed by mutually joining and fixing the lower absorbent sheet 21 and the upper absorbent sheet 21 by a hot melt type pressure sensitive adhesive the same as the adhesive 24, 25, and 26.

In the front reinforcing region 43 and the rear reinforcing region 44, the lower absorbent sheet 21 and the upper absorbent 22 are joined and fixed over whole faces thereof, by pressure sensitive adhesive thickly coated in the range of 20 to 60 g/m$^2$. The distance in the longitudinal direction between the border region 43*a* of the front reinforcing region 43 and the front end 20*a* of the absorbent body 20 is preferably in a range of 10 to 50 mm, and the distance in the longitudinal direction between the border region 44*a* of the rear reinforcing region 44 and the rear end 20*b* of the absorbent body 20 is preferably in a range of 10 to 50 mm.

A right peripheral region 23*a* and a left peripheral region 23*b* of the lower absorbent core 23 are shown by a broken line in FIG. 3. The width dimension of the lower absorbent core 23 is in a prescribed length range; to the front thereof, the right peripheral region 23*a* and the left peripheral region 23*b* slowly approach one another, and to the rear, the right peripheral region 23*a* and the left peripheral region 23*b* slowly approach one another.

The lower absorbent core 23 is formed of a layered body of pulp fiber enveloped in hydrophilic tissue paper, or is formed of a layered body of pulp fiber and highly absorbent resin enveloped in hydrophilic tissue paper. In a state in which the lower absorbent core 23 is sandwiched between the lower absorbent sheet 21 and the upper absorbent sheet 22, the lower absorbent sheet 21, the lower absorbent core 23, and the upper absorbent sheet 22 are pressurized together with heat applied, and are compressed. By this compression process, numerous embossed portions 27 are formed, as shown in FIG. 3. Each of the embossed portions 27 have small round shapes or square shapes, and are arrayed in the longitudinal direction and the lateral direction at intervals of, for example, 5 to 15 mm. Moreover, in addition to the embossed portions 27 or instead of forming the embossed portions 27, the lower absorbent sheet 21 and the lower absorbent core 23 may be joined by a hot melt type adhesive, and the lower absorbent core 23 and the upper absorbent sheet 22 may be joined by a hot melt type adhesive applied in a range that does not impede percolation of fluid.

The lower absorbent core 23 preferably has a weight of approximately 100 to 300 g/m$^2$, the embossed portions are made with a density in a range of 0.05 to 0.2 g/cm$^3$, and thickness thereof is in the rage of 0.5 to 5 mm. In the absorbent body 20, a region in which the lower absorbent sheet 21, the lower absorbent core 23, and the upper absorbent sheet 22 are layered (a region enclosed by the right peripheral portion 23a and the left peripheral portion 23b) is a main absorbent region 45. Moreover, the upper absorbent core 30 has a flat shape the same as the lower absorbent core 23 and has the same dimensions, and in the main absorbent region 45, the upper absorbent core 30 is piled directly above the lower absorbent core 23.

The width dimension of the main absorbent region 45 in the absorbent body 20 is from 20 to 50 mm, and the length dimension is approximately 80 to 160 mm. In the sanitary napkin 1, the main absorbent region 45 opposes the vaginal opening that is the female excretion area, and with the length dimension in the longitudinal direction being large, the main absorbent region 45 opposes an area from the vaginal opening to near the anus and farther, to the buttocks fissure area towards the rear.

As shown in FIG. 1 and FIG. 3, in this embodiment, the main absorbent region 45 is formed with the same distance range to the front and rear with a reference line X in the lateral direction of the sanitary napkin 1 as center. The reference line X in the lateral direction is a virtual line splitting the folded back flap portion 5 into a front part and a rear part. When the sanitary napkin 1 is worn, it is fitted with the shape of the folded back flap portion 5 and the pattern of the compressed portion 14 as indicators, so that the vicinity of the intersecting point of the reference line X in the lateral direction and the centerline Oy in the longitudinal direction coincides with the center of the vaginal opening.

As shown in FIG. 3, the right side buffer region 46 is between the main absorbent region 45 and the right side portion reinforcing region 41, and the left side buffer region 47 is between the main absorbent region 45 and the left side portion reinforcing region 42. The front buffer region 48 is between the main absorbent region 45 and the border region 43a, and the rear buffer region 49 is between the main absorbent region 45 and the border region 44a. As shown in FIG. 3, in the right side buffer region 46, the left side buffer region 47, the front buffer region 48, and the rear buffer region 49, a partial low density portion 50 is formed in at least one of the lower absorbent sheet 21 and the upper absorbent sheet 22. This low density portion 50 is formed by sandwiching the lower absorbent sheet 21 and the upper absorbent sheet 22 between gear shaped rolls that have a corrugated face, and by partially giving a tensile force to the sheets in the longitudinal direction and the lateral direction. Alternatively, instead of the low density portion 50, a cutout line may be formed in at least one of the lower absorbent sheet 21 and the upper absorbent sheet 22. The low density portion 50 or the cutout line are formed in a pattern of a short straight line shape, a crossed line shape, or the like, and, as shown in FIG. 3, are preferably disposed at intervals in the longitudinal direction.

Below, the right side portion reinforcing region 41 and the left side portion reinforcing region 42 are collectively referred to as side portion reinforcing regions, the front reinforcing region 43 and the rear reinforcing region 44 are collectively referred to as front and rear reinforcing regions, and the right side buffer region 46, the left side buffer region 47, the front buffer region 48, and the rear buffer region 49 are collectively referred to as buffer regions.

The bending stiffness in the lateral direction of the absorbent body 20 is lowest in the buffer regions, and the bending stiffness of the right side buffer region 46, the left side buffer region 47, the front buffer region 48, and the rear buffer region 49 are about equal. The bending stiffness of the side portion reinforcing regions is greater than that of the buffer regions; the bending stiffness of the front and rear reinforcing regions is greater than that of the buffer regions, and the bending stiffness of the main absorbent region is greater than that of the buffer regions. Preferably, the relationship of bending stiffness of the regions is expressed as: the side portion reinforcing regions>the front and rear reinforcing regions>the main absorbent region>the buffer regions; or the side portion reinforcing regions>the main absorbent region>the front and rear reinforcing regions>the buffer regions.

The bending stiffness is defined as follows. Test samples are made, the same structure being used for the side portion reinforcing regions, the front and rear reinforcing regions, the main absorbent region, and the buffer regions, and each sample has the same width dimension in the lateral direction, and length dimension in the longitudinal direction. These test samples are held and supported at one end and the size of a force necessary to cause a flexural deformation of the free end in a lateral direction corresponds to the size of the bending stiffness. Specifically, the test samples are made so as to have a width dimension of 25 mm and a length dimension of 38 mm; a "Gurley Bending Resistance Tester" manufactured by Yasuda Seiki Seisakusho, Ltd, is used, the test sample is fixed to the tester at a position 6.3 mm from the end thereof in the long direction, a pendulum to which a spindle is attached is passed to a position 25 mm distant from the fixed portion of the test sample, and the stiffness is a value measured by the tester of the force the pendulum requires to spring the test sample.

The bending stiffness in the lateral direction of the side portion reinforcing regions is preferably 3.92 mN (400 mg) or greater, and the bending stiffness in the lateral direction of the front and rear reinforcing regions is preferably 3.92 mN (400 mg) or greater. The upper limit of the bending stiffness of these reinforcing regions is preferably approximately 7.84 mN (800 mg). The bending stiffness of the buffer regions is preferably less than 3.92 mN (400 mg), and is more preferably less than 2.94 mN (300 mg). The lower limit of the bending stiffness of the buffer regions is approximately 0.98 mN (100 mg). Furthermore, the difference in the bending stiffness of the main absorbent region 45 and the buffer regions is preferably 1.47 mN (150 mg) or greater.

If the bending stiffness of the side portion reinforcing regions is 3.92 mN (400 mg) or greater, when the absorbent article 20 receives the compressive force in the lateral direction from the thigh areas, in a state in which it is worn in the groin area, the right side portion reinforcing region 41 and the left side portion reinforcing region 42 easily deform in a curve towards the centerline Oy in the longitudinal direction, and when the pressurizing force from the thigh areas is removed, the absorbent article 20 easily recovers to its original shape. If the difference between the bending stiffness of the main absorbent region 45 and the buffer regions is 1.47 mN (150 mg) or greater, when the right side portion reinforcing region 41 and the left side portion reinforcing region 42 deform and curve towards the centerline Oy in the longitudinal direction, the right side buffer region 46 and the left side buffer region 47 compress, the pressurizing force acting on the main absorbent region 45 is relaxed, and the main absorbent region 45 does not easily deform.

The upper absorbent core 30 shown in FIG. 2 is positioned directly above the lower absorbent core 23, and is disposed so as not to overlap with the buffer regions. The absorbent core 30 may be fixed and joined to the upper absorbent sheet 22 via a hot melt type adhesive applied with a coating amount that does not impede permeation of fluid, and it may be positioned so as not to move, by being enclosed by the above described compressed portion 14.

The upper absorbent core 30 has a pulp layer 31 that can absorb and retain fluids. The pulp layer 31 is composed of pulp fiber and highly absorbent resin, with a weight of approximately 200 to 400 g/m$^2$. The pulp layer 31 is enveloped by a cover layer 32. The cover layer 32 is permeable to fluids, and, for example, is formed of a core-in-sheath composite synthetic fiber with a core of PET resin and a sheath of PE resin, with a weight of approximately 20 to 50 g/m$^2$, and is a through-air non-woven fabric with a density of approximately 0.01 to 0.05 g/cm$^3$. Alternatively, the cover layer may be of hydrophilic tissue paper.

The lower face of the upper absorbent core 30 (the face that opposes the upper absorbent sheet 22) and both the left and right side faces are covered by a permeating-fluid controlling sheet 33. The permeating-fluid controlling sheet 33 does not allow excessive migration of fluid, that is passed to the pulp layer 31, to the absorbent body 20, and performs control so that fluid can be retained within the pulp layer 31, and when the amount of fluid within the pulp layer 31 exceeds the fluid absorptive capacity of the pulp layer 31, controls flow to pass that fluid to the absorbent body 20. It also has a capability to restrain the fluid retained in the pulp layer 31 from flowing out to the two external sides of the upper absorbent core 30. Moreover, a skin-side face of the pulp layer 31 is not covered by the permeating-fluid controlling sheet 33.

The permeating-fluid controlling sheet 33 is composed of a plurality of piled layers of fluid-permeable non-woven fabric, or resin film in which a large number of fluid permeable pores are formed, or is formed of laminated material of resin film and non-woven fabric, or the like.

The top sheet 11 may be of any type, as long as it is hydrophilic and fluid permeable. For example, the top sheet 11 may be formed of a through-air non-woven fabric, a spunbond non-woven fabric, a spunlace non-woven fabric, or a non-woven fabric with a large number of fluid-permeable pores, a resin film in which a large number of fluid-permeable pores are formed, a laminated material of a resin film, in which a large number of fluid-permeable pores are formed, and a fluid-permeable non-woven fabric, or the like. The side sheets 12 are formed of resin film in which a large number of fluid-permeable pores are formed, a spunbond non-woven fabric having fluid-permeable pores, or the like.

The back sheet 13 blocks off fluids, and is formed of a resin film made of PE resin or PP resin. Alternatively, it may be an air-permeable resin film including a minute filler, with small pores, formed around the filler, that are air-permeable but impermeable to fluids.

FIG. 5 is a plan view showing the back sheet 13 only, and FIG. 6 is a sectional view corresponding to a section along a line VI-VI of FIG. 5, showing a state with the absorbent body 20 and the back sheet 13 joined.

As shown in FIG. 6, the back sheet 13 and the lower absorbent sheet 21 of the absorbent body 20 are joined and fixed by a hot melt type pressure sensitive adhesive 55. In the actual joining, the adhesive 55 is applied in a pattern shown in FIG. 5 to the garment side face of the lower absorbent sheet 21, and the lower absorbent sheet 21 and the back sheet 13 are joined and fixed.

The application pattern of the adhesive 55 has a fine application region 56 and a coarse application region 57. Regarding the adhesive 55, the application density of the fine application region 56 is higher than that of the coarse application region 57. For example, in the fine application region 56, the adhesive 55 is applied to a face at an application amount of 30 to 50 g/m$^2$. In the coarse application region 57, the adhesive 55 is applied in a spiral shape at an application amount of 5 to 15 g/m$^2$. Alternatively, in the coarse application region 57, the adhesive 55 is applied in a comb-tooth shaped, wave shaped, or dot-shaped pattern.

The coarse application region 57 is formed mainly from the right side buffer region 46, to below the rear buffer region 49, and from the left side buffer region 47 to below the rear buffer region 49. In the buffer regions, in the border of the joint of the lower absorbent sheet 21 and the back sheet 13, fiber, of which the lower absorbent sheet 21 is composed, can move easily. Conversely, in the right side portion reinforcing region 41, the left side portion reinforcing region 42, the front reinforcing region 43, the rear reinforcing region 44, and the main absorbent region 45, since the lower absorbent sheet 21 and the back sheet 13 are joined over complete faces, the fiber does not move easily. By this type of composition, the bending stiffness of the buffer regions can be arranged to be low, and the bending stiffness of the main absorbent region 45 and the respective reinforcing regions can be set to be high.

The sanitary napkin 1 is attached and fixed to an inner face of the crotch area of underwear via the pressure sensitive adhesive layer 15 provided on the garment side face of the back sheet 13; the folded back flap portions 5 and 5 are folded back so as to sandwich both side peripheral portions of the crotch area of the underwear; and the folded back flap portions 5 and 5 are attached and fixed to an external face of the underwear, by the flap portions pressure sensitive adhesive layer 16.

The width dimension, when the sanitary napkin 1 is fixed to the crotch area of the underwear, approximately matches the width dimension of the absorbent body 20, and this width dimension is approximately 50 to 100 mm. On the other hand, the width of a female's groin area, that is, the minimum value of the distance between the two thigh areas, is approximately 20 to 40 mm. Accordingly, when a wearer's body moves in a state with the sanitary napkin 1 worn in the groin area, a compressive force acts from both left and right sides towards the centerline Oy in the longitudinal direction, against the sanitary napkin 1. FIG. 7 (A) shows the absorbent body 20 before the compressive force acts, and FIG. 7 (B) schematically shows the absorbent body 20 when the compressive force is acting.

As shown in FIG. 7 (B), the compressive force from the thigh areas acts on the right side portion reinforcing region 41 and the left side portion reinforcing region 42. The bending stiffness of the right side portion reinforcing region 41 and the left side portion reinforcing 5 region 42 in the lateral direction is high, and moreover, the right side portion reinforcing region 41 and the left side portion reinforcing region 42 are connected at the front by the front reinforcing region 43, and are connected at the rear by the rear 10 reinforcing region 44. Since the bending stiffness of the front reinforcing region 43 and the rear reinforcing region 44 is high, deformation in which the whole of the right side portion reinforcing region 41 and left side portion reinforcing region 42 approach one another does not easily occur.

In the absorbent body 20, the main absorbent region 45, in which the lower absorbent core 23 is provided, has a higher bending stiffness than the right side buffer region 46 and the left side buffer region 47, and the stiffness is even higher where the upper absorbent core 30 is additionally piled on top of the main absorbent region 45 of the absorbent body 20. As a result, when the right side portion reinforcing region 41 and the left side portion reinforcing region 42 bend, the right side buffer region 46 and the left side buffer region 47 are compressed and deform easily, the compressive force acting on the main absorbent region 45 is relaxed, the main absorbent region 45 is not compressed, or if compressed, the decrease in the width dimension is only a little. Thus, the main absorbent region 45 consistently and easily has a tight fit to the vaginal opening over a wide area.

Figure 7A:
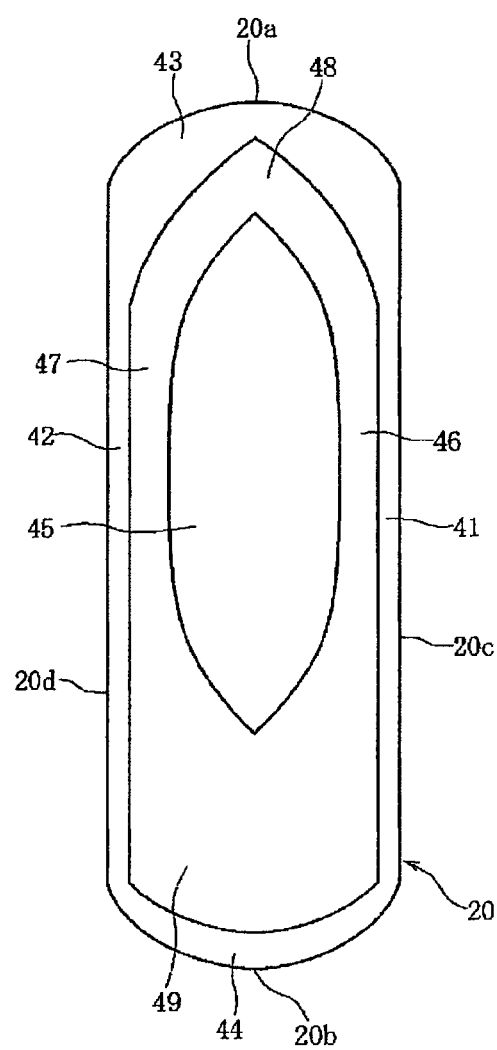
FIGS. 7 (A) and (B) are explanatory views showing deformation characteristics of the sanitary napkin.
Figure 7B:
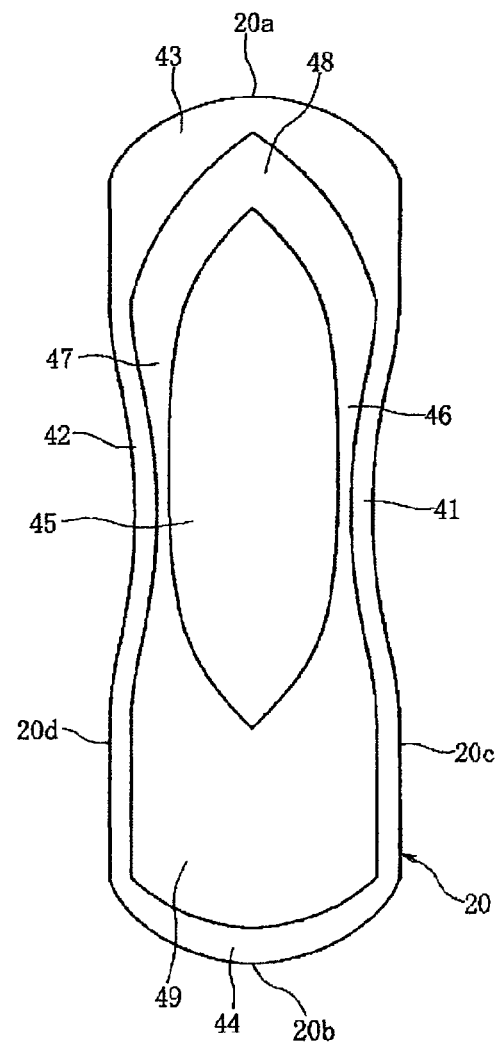

When the compressive force from the thigh areas is released, by the elastic restorative power of the right side portion reinforcing region 41 and the left side portion reinforcing region 42, the absorbent body 20 easily returns to its original shape or dimensions as shown in FIG. 7(A). In particular, with the presence of the front reinforcing region 43 and the rear reinforcing region 44, when the compressive force is released, the deformed state in which the width of the overall absorbent body 20 is narrowed is not supported, and recovery to an extended overall width dimension is facilitated. For example, if the underwear is pulled down when the sanitary napkin 1 is being used, since the absorbent body 20 easily recovers to a state shown in FIG. 7 (A), the wearer, when she sees that the sanitary napkin 1 is in its widened state, is given a sense of ease that leakage of menstrual blood in the lateral directions has not occurred.

Next, other embodiments of the present invention are explained. In the embodiment described below, constituent parts that are the same as the sanitary napkin 1 in the first embodiment are given the same reference symbols as the sanitary napkin 1 and detailed explanations thereof are omitted.

Figure 8A:
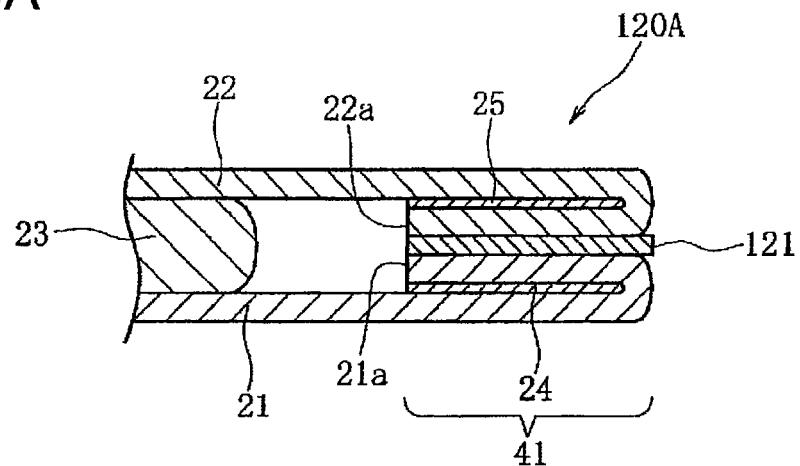
FIGS. 8 (A), (B), and (C) are partial sectional views showing other embodiments of the absorbent body used in the sanitary napkin according to the first embodiment.
Figure 8B:
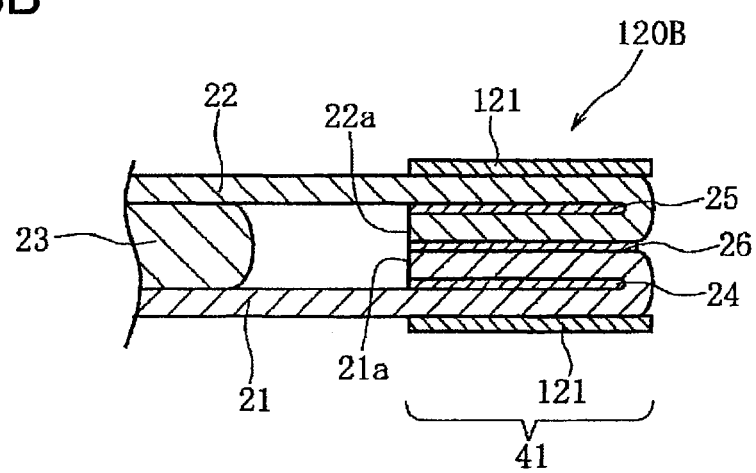
Figure 8C:
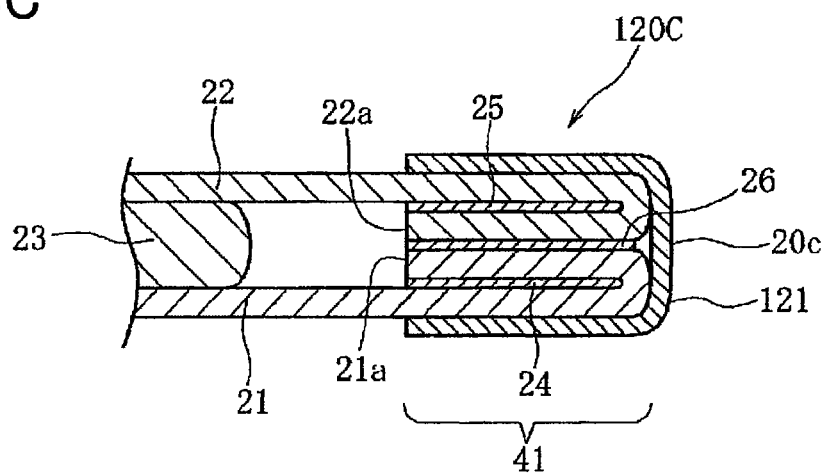

FIGS. 8 (A), (B), and (C) are partial sectional views showing other embodiments of the side of the absorbent body, that is, the composition of the right side portion reinforcing region 41.

In the absorbent body 120A shown in FIG. 8 (A), a reinforcing sheet 121 is sandwiched between a folded back portion of a lower absorbent sheet 21 and a folded back portion of an upper absorbent sheet 22, and both folded back portions and a reinforcing sheet 121 are joined by a hot melt type pressure sensitive adhesive layer. The reinforcing sheet 121 is a fluid permeable sheet including a synthetic resin in at least one portion thereof. If the reinforcing sheet 121 is formed of the fluid permeable sheet including the synthetic resin, even if menstrual blood is passed to a right side portion reinforcing region 41 and it is in a moist state, the bending stiffness of the right side portion reinforcing region 41 does not easily deteriorate. The reinforcing sheet 121 is also provided at a left side portion reinforcing region 42. In addition, in a front reinforcing region 43 and a rear reinforcing region 44, the reinforcing sheet 121 may also be sandwiched between the lower absorbent sheet 21 and the upper absorbent sheet 22.

The reinforcing sheet 121 is a non-woven fabric composed of a fiber formed of PE, PP, or PET resin, or of a composite synthetic fiber formed of two types of these resins, or a non-woven fabric in which a large number of fluid permeable pores are formed. Alternatively, it may be a resin film with a thickness of approximately 0.5 to 1.5 mm and a weight of 20 to 35 g/m$^2$, in which a large number of fluid permeable pores are formed.

In an absorbent body 120B shown in FIG. 8 (B), the reinforcing sheet 121 is placed on and attached to each of the lower face of the folded back portion of the lower absorbent sheet 21 and the upper face of the folded back portion of the upper absorbent sheet 22. In an absorbent body 120C shown in FIG. 8 (C), the reinforcing sheet 121 is arranged to cover the bottom face of the lower absorbent sheet 21, the edge of the absorbent body 20, and the upper face of the upper absorbent sheet 22, and is attached thereto. As shown in FIG. 8 (C), when the edge of the absorbent body 20 is covered by the reinforcing sheet 121, by the fluid permeability capability of this reinforcing sheet 121 being decreased a little, menstrual blood that is absorbed by the absorbent body 20 is easily prevented from leaking out to the sides.

Figure 9A:
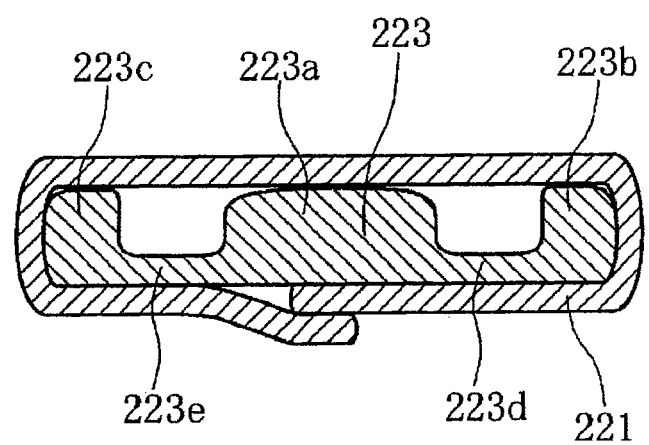
FIGS. 9 (A) and (B) are sectional views showing a manufacturing process for an absorbent body according to a second embodiment.
Figure 9B:
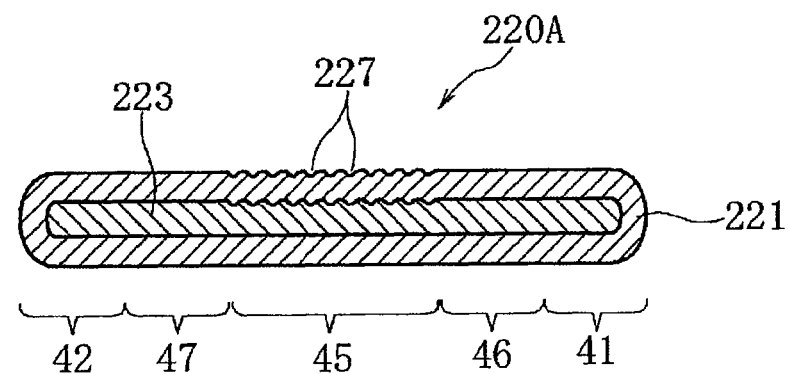

FIGS. 9 (A) and (B) are sectional views showing a manufacturing process for an absorbent body 220A according to a second embodiment. As shown in FIG. 9(A), a lower absorbent core 223 that forms an absorbent body 220A is a mixed layer of pulp fiber and highly absorbent resin, a mixed layer of pulp fiber, rayon fiber, and highly absorbent resin, or a mixed layer of pulp fiber, synthetic resin fiber, and highly absorbent resin. The lower absorbent core 223 is composed with a high weight in a portion 223a corresponding to the main absorbent region, a portion 223b corresponding to the right side portion reinforcing region, a portion 223c corresponding to a left side portion reinforcing region; and a low weight in portions 223d and 223e corresponding to the buffer regions. Furthermore, the lower absorbent core 223 is enveloped by a covering sheet 221 that is hydrophilic and fluid permeable. The covering sheet 221 is composed of a non-woven fabric including a synthetic resin fiber as in through-air non-woven fabric. If the covering sheet 221 that includes the synthetic resin fiber is used, when the absorbent body 220A is moist, the overall bending stiffness can be increased. However, the covering sheet 221 may be composed of another non-woven fabric or hydrophilic tissue paper.

The covering sheet 221 and the lower absorbent core 223 shown in FIG. 9 (A) are compressed in the direction of thickness, and additionally, in the portion that is the main absorbent region 45, the covering sheet 221 and the lower absorbent core 223 are compressed in an embossed portion 227 to form a absorbent body 220A shown in FIG. 9 (B). In the absorbent body 220A shown in FIG. 9 (B), the bending stiffness of the right side portion reinforcing region 41 and the left side portion reinforcing region 42 can be made higher than the bending stiffness of the right side buffer region 46 and the left side buffer region 47, and the bending stiffness of the main absorbent region 45 can also be made higher than the bending stiffness of the buffer regions 46 and 47.

Figure 10A:
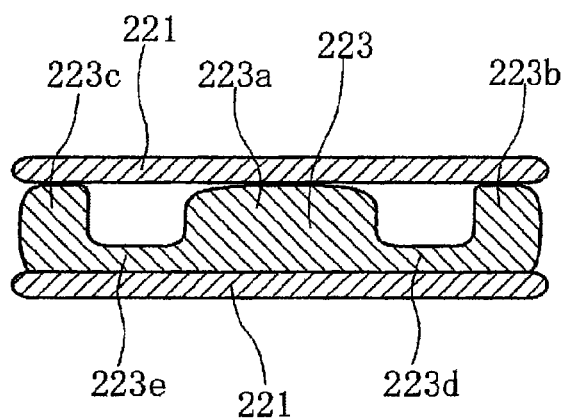
FIGS. 10 (A) and (B) are sectional views showing a manufacturing process for a modified example of the absorbent body according to the second embodiment.
Figure 10B:
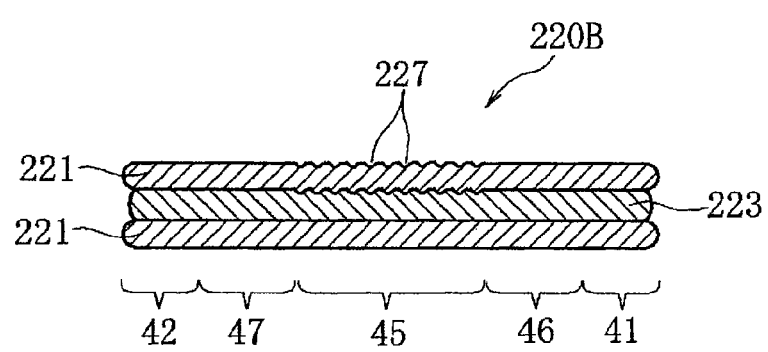

FIG. 10 (B) is a sectional view showing an absorbent body 220B. The lower absorbent core 223 shown in FIG. 10 (A) is the same as that shown in FIG. 9 (A), and the covering sheets 221 and 221 are individually placed on the lower face and the upper face of the lower absorbent core 223. By compressing in the direction of thickness, the absorbent body 220B is formed.

Figure 11:
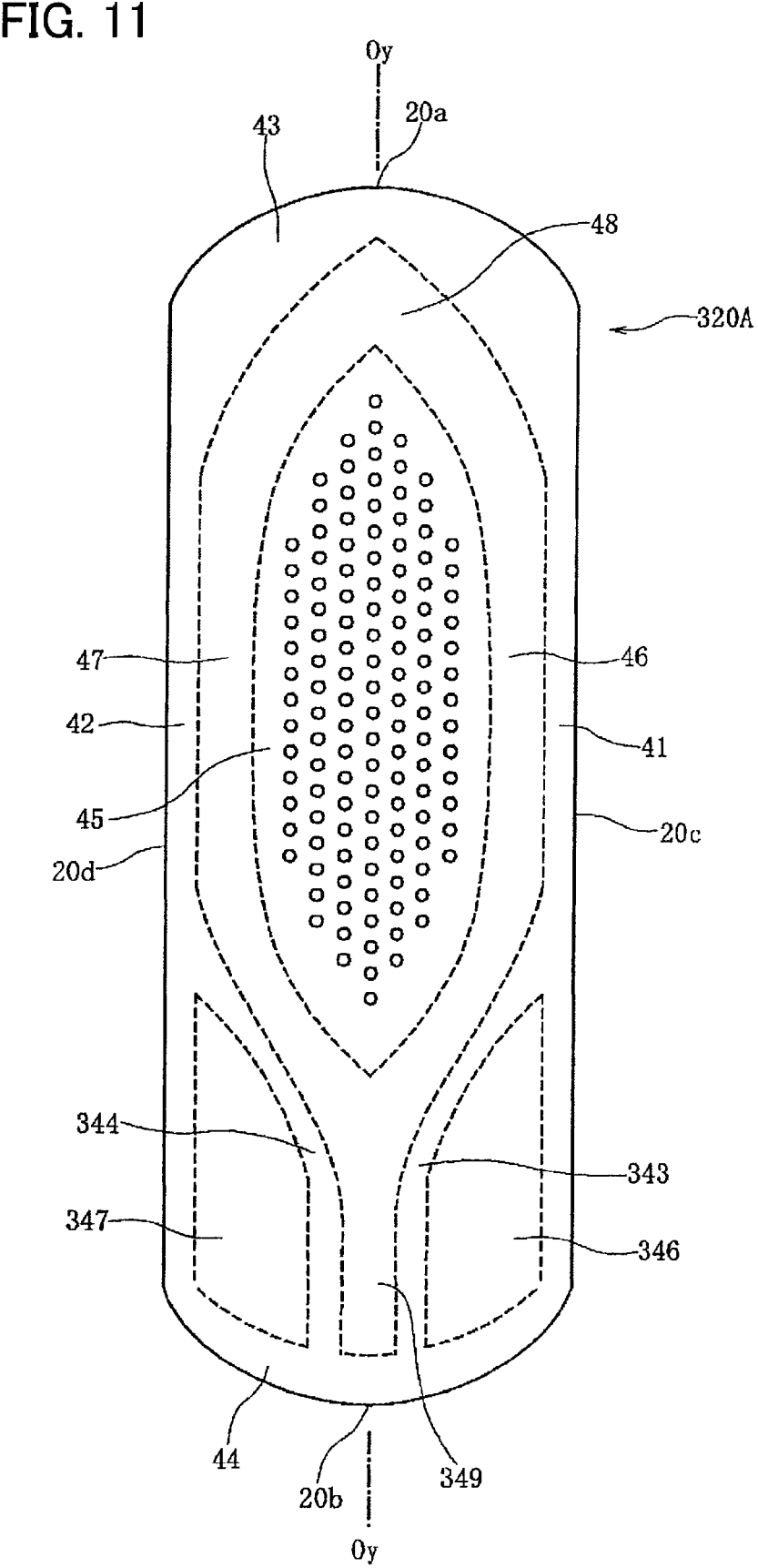
FIG. 11 is a plan view showing an absorbent body according to a third embodiment of the present invention.

FIG. 11 is a plan view showing an absorbent body 320A used in a sanitary napkin according to a third embodiment. This absorbent body 320A is composed of a lower absorbent sheet 21, an upper absorbent sheet 22, and a lower absorbent core 23, the same as the absorbent body 20 shown in FIG. 3 and FIG. 4. Furthermore, the two side portions of the lower absorbent sheet 21 are folded back, the two side portions of the upper absorbent sheet 22 are folded back and are mutually joined with an adhesive, and the right side portion reinforcing region 41 and the left side portion reinforcing region 42 are formed. The lower absorbent core 23 is arranged on the main absorbent region 45, and in the front reinforcing region 43 and the rear reinforcing region 44 the lower absorbent sheet 21 and the upper absorbent sheet 22 are joined by a pressure sensitive adhesive and are fixed.

In this absorbent body 320A, intermediate reinforcing regions 343 and 344 are arranged to the rear of the main absorbent region 45. The intermediate reinforcing region 343 extends from the right side portion reinforcing region 41 towards the inside, and, with a distance from the main absorbent region 45 provided, is continuous with the rear reinforcing region 44. The other intermediate reinforcing region 344 extends from the left side reinforcing region 42 towards the inside, and, with a distance from the main absorbent region 45 provided, is continuous with the rear reinforcing region 44. A portion enclosed by the two intermediate reinforcing regions 343 and 344, the main reinforcing region 45, and the rear reinforcing region 44 is a rear buffer region 349. Moreover, a portion enclosed by the right side portion reinforcing region 41, the intermediate reinforcing region 343, and the rear reinforcing region 44 is a rear buffer region 346; and a portion enclosed by the left side portion reinforcing region 42, the intermediate reinforcing region 344, and the rear reinforcing region 44 is a rear buffer region 347.

The intermediate reinforcing region 343 and the intermediate reinforcing region 344 are formed by fixing and joining the lower absorbent sheet 21 and the upper absorbent sheet 22 via a pressure sensitive adhesive. Furthermore, they are formed by interposing and attaching the reinforcing sheet 121 shown in FIGS. 8 (A), (B), and (C). Alternatively, the formation may also be realized by increasing the weight of at least one of the lower absorbent sheet 21 and the upper absorbent sheet 22.

By providing the intermediate reinforcing regions 343 and 344, the bending stiffness in the lateral direction of the rear region of the absorbent body 320A can be increased. Thus, in cases in which the wearer crosses her legs while in a seated position with the sanitary napkin worn, and a twisting force acts on the absorbent body 320A, the absorbent body 320A easily recovers from a twisted state to its original shape. Furthermore, in the rear portion of the absorbent body 320A, since the right side portion reinforcing region 41, the rear buffer region 346, the intermediate reinforcing region 343, the rear buffer region 349, the intermediate reinforcing region 344, the rear buffer region 347, the left side portion reinforcing region 42 are alternately disposed, in the lateral direction, that is, portions with high bending stiffness and portions with low bending stiffness are alternately disposed, the rear portion of the absorbent body 320A easily deforms to follow the round face of the buttocks.

Moreover, the intermediate reinforcing region 343 and the intermediate reinforcing region 344 are disposed to the left and right, at a distance from the centerline Oy in the longitudinal direction, and since the soft rear buffer region 349 is positioned on the centerline Oy in the longitudinal direction, the rear buffer region 349 deforms easily so as to enter the anus recession and inside the buttocks fissure area.

Figure 12:
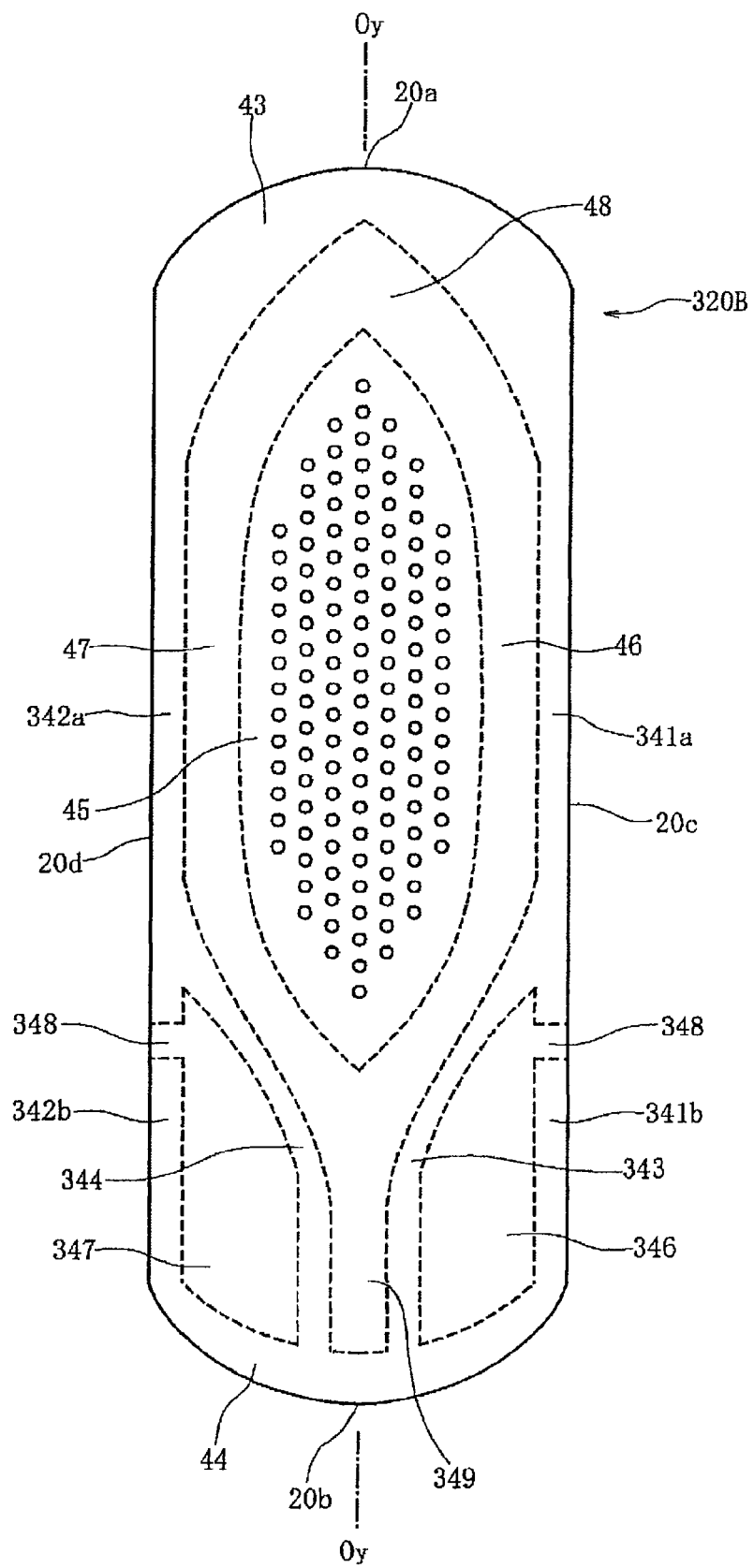
FIG. 12 is a plan view showing a modified example of the absorbent body according to the third embodiment of the present invention.

An absorbent body 320B shown in FIG. 12 is a modified example of the absorbent body 320A of the third embodiment. In the absorbent body 320B shown in FIG. 12, a right side portion reinforcing region 341a is formed towards the front, on the right side portion, a right side portion reinforcing region 341b is formed towards the rear, and in between them, a discontinuous portion 348 is formed. In the left side portion of the absorbent body 320B, a left side portion reinforcing region 342a is formed towards the front, a left side portion reinforcing region 342a is formed to the rear, and in between them, a discontinuous portion 348 is formed. The discontinuous portions 348 have a bending stiffness that is lower than that of each of the side portion reinforcing regions. The intermediate reinforcing region 343 is formed so as to be connected to the right side portion reinforcing region 341a positioned towards the front and the rear reinforcing region 44, and the intermediate reinforcing region 344 is formed so as to be connected to the left side portion reinforcing region 342a positioned towards the front and the rear reinforcing region 44.

In the absorbent body 320B described above, the discontinuous portions 348 are formed at the right side portion reinforcing regions and the left side portion reinforcing regions; these discontinuous portions 348 are arranged more to the rear than the reference line X in the lateral direction. As a result, deformation due to the compressive force that acts on the front portion from the thigh areas is cut off by the discontinuous portions 348 and is not easily transmitted to the rear, so that compressive deformation of the rear portion of the absorbent body 320B can be curtailed. Accordingly, the rear portion of the absorbent body 320B is easily fitted tightly to a wearer's body in a widened state. Moreover, the present invention is not limited to the above described embodiments.

In each of the above described embodiments, the side portion reinforcing regions, the main absorbent region, and the buffer regions are formed in the absorbent body; however, the side portion reinforcing regions, the main absorbent region, and the buffer regions need not be formed in an absorbent body. For example, instead of the lower absorbent sheet 21 and the upper absorbent sheet 22, a low density non-woven fabric or the like can be used, which, although its capability for retained fluid is low, can diffuse fluid and allow it to pass through.

Furthermore, in between the back sheet 13 and the top sheet 11 of the sanitary napkin, a fluid absorbent layer may be provided in the main absorbent region 45; side portion reinforcing members extending in the longitudinal direction may be provided at positions to the left and right, separated from the fluid absorbent layer, to form side portion reinforcing regions; a front reinforcing member connecting the side portion reinforcing members may be provided at a separated position to the front of the fluid absorbent layer, to form a front reinforcing region; and a rear reinforcing member connecting the side portion reinforcing members may be provided at a separated position to the rear of the fluid absorbent layer, to form a rear reinforcing region. In this way, a formation is possible in which the main absorbent region and each of the reinforcing regions are separate bodies. In these cases, the buffer regions are formed by the back sheet and the top sheet. Alternatively, the buffer regions may be formed by interposing a soft non-woven fabric or the like, between the back sheet and the top sheet. The reinforcing members are formed of air-laid non-woven fabric, thick non-woven fabric, resin foam, or the like.

EMBODIMENT

The main absorbent region, the side portion reinforcing regions, the front reinforcing region, the rear reinforcing region, and the buffer regions are formed by the absorbent body. The lower absorbent sheet and the upper absorbent sheet shown in FIG. 3 and FIG. 4 are used in the absorbent body. The lower absorbent sheet and the upper absorbent sheet are formed of air-laid non-woven fabric with a weight of 80 g/m$^2$, a density of 0.08 g/cm$^3$, and including 65% mass pulp fiber, 30% mass synthetic resin fiber, and 5% mass acryl-based binder. Both sides of the upper absorbent sheet and the lower absorbent sheet are each folded so that the width dimension is 5 mm, and the inner faces of the folded sheets are attached to each other by an acryl-based hot melt type pressure sensitive adhesive. The applied amount of the adhesive is 30 g/m². In addition, as in the embodiment of FIG. 4, the folded back portion of the lower absorbent sheet and the folded back portion of the upper absorbent sheet are attached using the pressure sensitive adhesive (applied at an amount of 30 g/m²), to form the side portion reinforcing regions.

The front reinforcing region and the rear reinforcing region are formed by attaching the upper absorbent sheet and the lower absorbent sheet, using the pressure sensitive adhesive (applied at an amount of 30 g/m²), at a range of 10 mm to the inside from the front edge of the lower absorbent sheet and the upper absorbent sheet, and a range of 10 mm to the inside from the rear edge.

The absorbent core is sandwiched between the lower absorbent sheet and the upper absorbent sheet to form the main absorbent region. The absorbent core is formed with a weight of 200 g/m², including 90% mass pulp fiber and 10% mass highly absorbent resin, with a pressure of 3920 Kpa (40 kgf/cm²) being applied at a temperature of 95 degrees Celsius for one second.

Between the main absorbent region and both left and right side portion reinforcing regions, a buffer region made of the lower absorbent sheet and the upper absorbent sheet is formed; and between the main absorbent region and the front reinforcing region, and between the main absorbent region and the rear reinforcing region, a buffer region made from the lower absorbent sheet and the upper absorbent sheet is formed. In each of the buffer regions, each of the lower absorbent sheet and the upper absorbent sheet are partially stretched using a roller having a gear shape, to form a low density portion with a large number of repeated shapes. The low density portion is formed of an array of perforation shapes, with a width of 1 mm and a length of 3 mm, at 2 mm intervals in the longitudinal direction, the perforations being made at 3 mm intervals in the lateral direction.

The lower absorbent sheet, the upper absorbent sheet, and the absorbent core are sandwiched between the back sheet and the top sheet; and each material is fixed to the back sheet and to the top sheet by a hot melt type adhesive applied at 3 g/m². The back sheet is formed of polyethylene resin film with a weight of 23.5 g/m², and the top sheet is formed of a polyethylene resin film with many fluid-permeable pores so as to have an aperture ratio of 27% at a weight of 25 g/m². This polyethylene resin film includes 1% mass of a hydrophilic agent.

The external form of the absorbent body forming the above described side portion reinforcing regions, the front reinforcing region, the rear reinforcing region, and in addition, above described buffer region, and the external form of the main absorbent region are approximately the same as the embodiment shown in FIG. 1 and FIG. 3, and the length dimension from the front edge of the overall absorbent body to the rear edge is 230 mm, and the width dimension is 75 mm. The main absorbent region has a length dimension of 80 mm and a width dimension or 35 mm. The overall sanitary napkin has a length dimension of 260 mm, and a width dimension at the folded back flap of 150 mm.

The Gurley stiffness value for bending in the lateral direction is b 4.9 mN (500 mgf) for the side portion reinforcing regions, 3.14 mN (320 mgf) for the front reinforcing region and the rear reinforcing region, and 1.54 mN (162 mgf) for the buffer regions. These bending stiffness values are measured for test samples having a structure the same as each of the regions, with a width dimension of 25 mm and a length dimension of 38 mm, using the abovementioned Gurley Bending Resistance Tester, manufactured by Yasuda Seiki Seisakusho, Ltd.

COMPARATIVE EXAMPLE 1

A conventional sanitary napkin is used, having an absorbent body formed of a laminated pulp fiber body that has a uniform overall thickness. Both side portions of the absorbent body are cut with a width dimension of 25 mm and a length dimension of 38 mm, and the bending stiffness (Gurley stiffness value) measured in the lateral direction is 5.15 mN (526 mgf).

COMPARATIVE EXAMPLE 2

A conventional sanitary napkin is used, having an absorbent body formed of an air-laid non-woven fabric formed of pulp fiber and an acryl-based binder, having a uniform overall thickness. Both side portions of the absorbent body are cut with a width dimension of 25 mm and a length dimension of 38 mm, and the bending stiffness (Gurley stiffness value) measured in the lateral direction is 1.95 mN (199 mgf).

COMPARITIVE EXAMPLE 3

A test sample of a sanitary napkin is made, having a front reinforcing region and a rear reinforcing region, but not having side portion reinforcing regions. The first embodiment with both side portion reinforcing regions removed is made the comparative example 3.

Experimental Method

The embodiment and the comparative example are worn at the inner face of the crotch portion of sanitary briefs, the sanitary briefs are worn on the lower body of a doll that is made of acryl resin and that can move, and the two thigh areas are moved the same as if walking at a speed of 20 m/minute. After performing the moving for one minute, 5 milliliters of artificial menstrual blood is passed at feed rate of 7 milliliters per minute to the embodiment and the comparative example, and the doll is moved for a further 30 minutes.

Experimental Results

The embodiment exhibited almost no twists or wrinkles, and, after the experiment, recovered to approximately the original shape. In the comparative example 1 there were few twists or wrinkles, due to using a thick absorbent body; however, there was a deformation in that the centerline in the longitudinal direction exhibited a convex shape in the direction of the top sheet, and the absorbent body could not recover to its original shape after the experiment. In the comparative examples 2 and 3, twists and wrinkles occurred in the absorbent body after the experiment, the width dimension of the central portion in the longitudinal direction of the absorbent body was narrowed, and recovery was not realized.

Furthermore, the artificial menstrual blood was composed from 320 g of glycerin (manufactured by Wako Pure Chemical Industries, Ltd.), 32 g of carboxymethyl cellulose sodium salt (manufactured by Wako Pure Chemical Industries, Ltd.), 16 g of sodium chloride (manufactured by Wako Pure Chemical Industries, Ltd.), 16 g of sodium acid carbonate (manufactured by Wako Pure Chemical Industries, Ltd.), certified colorants (manufactured by Koyo Products Ltd.) including 312 g of red No. 102, 8 g of red No. 2, 8 g of yellow No. 5, and in addition 4 liters of ion exchanged water, and this artificial menstrual blood with a viscosity of 22 to 26 mPa·s was used.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article, worn in a wearer's groin area, having a longitudinal direction in a lengthwise orientation and a lateral direction in a direction orthogonal to the longitudinal direction, the article comprising:
    an upper absorbent core;
    an absorbent body having a main absorbent region including a lower absorbent core, positioned on a centerline in the longitudinal direction, wherein the absorbent body further includes an upper absorbent sheet and a lower absorbent sheet, the lower absorbent core is interposed between the upper absorbent sheet and the lower absorbent sheet;
    a top sheet that is permeable to fluids, covering a skin-side face of the absorbent body;
    a back sheet covering a garment-side face of the absorbent body;
    buffer regions positioned around the main absorbent region and forming a part of the absorbent body, wherein said buffer regions have a stiffness lower than that of the main absorbent region and include perforations formed in at least one of the upper and lower absorbent sheets, said perforations extending discontinuously along the longitudinal direction thereof;
    side portion reinforcing regions with stiffness larger than the buffer regions, positioned at left and right external sides of the buffer regions and extending in the longitudinal direction, wherein the side portion reinforcing regions are formed by folding left and right side ends of upper and lower absorbent sheets inwardly, and bonding the folded side ends to each other; and
    a front reinforcing region and a rear reinforcing region whose bending stiffness in the lateral direction is larger than that of the buffer regions, positioned at front and rear external sides of the buffer regions, connecting continuously, among the side portion reinforcing regions, a left side portion reinforcing region and a right side portion reinforcing region, so that the left side portion and the right side portion do not easily approach one another, and easily recover to their shape.

2. An absorbent article according to claim 1,
    wherein the buffer regions include a front buffer region positioned between the main absorbent region and the front reinforcing region, and a rear buffer region positioned between the main absorbent region and the rear reinforcing region.

3. An absorbent article according to claim 1, wherein the main absorbent region, the buffer regions, and the side portion reinforcing regions are formed in the absorbent body.

4. An absorbent article according to claim 2, wherein the main absorbent region, the buffer regions, the side portion reinforcing regions, the front reinforcing region, and the rear reinforcing region are formed in the absorbent body.

5. An absorbent article according to claim 4, wherein, in the side portion reinforcing regions, the absorbent sheets are folded, and the absorbent sheets are fixed together by an adhesive.

6. An absorbent article according to claim 1, wherein, in the absorbent body, the weight of the side portion reinforcing regions is larger than that of the buffer regions, and the weight of the main absorbent region is larger than that of the buffer regions.

7. An absorbent article according to claim 6, wherein the absorbent body is compressed in a direction of thickness.

8. An absorbent article according to claim 6, wherein, in the main absorbent region, the upper absorbent core is laid upon the absorbent body.

9. An absorbent article according to claim 1, wherein plural absorbent sheets are fixed via an adhesive in the front reinforcing region and the rear reinforcing region.

10. An absorbent article according to claim 1, wherein the absorbent body is reinforced by a reinforcing sheet including thermoplastic resin in the side portion reinforcing regions.

11. An absorbent article according to claim 1, further comprising an intermediate reinforcing region arranged, among the side portion reinforcing regions, between a left side portion reinforcing region and a right side portion reinforcing region, to the rear of the main absorbent region, the buffer regions being arranged between the intermediate reinforcing region and the side portion reinforcing regions.

12. An absorbent article according to claim 1, wherein the side portion reinforcing regions have a discontinuous portion in the rear region, the bending stiffness in the lateral direction being smaller in the discontinuous portion than in the side portion reinforcing regions.

13. An absorbent article according to claim 3, wherein the absorbent body and the back sheet are fixed via an adhesive, and wherein an application amount, per unit area, of the adhesive at the side portion reinforcing regions is larger than that at the buffer regions, and the application amount of the adhesive, per unit area, of the main absorbent region is larger than that of the buffer regions.

14. An absorbent article, worn in a wearer's groin area, having a longitudinal direction in a lengthwise orientation and a lateral direction in a direction orthogonal to the longitudinal direction, the article comprising:
    an upper absorbent core;
    an absorbent body having a main absorbent region including a lower absorbent core, positioned on a centerline in the longitudinal direction, wherein the absorbent body further includes an upper absorbent sheet and a lower absorbent sheet, the lower absorbent core is interposed between the upper absorbent sheet and the lower absorbent sheet;
    a top sheet that is permeable to fluids, covering a skin-side face of the absorbent body;
    a back sheet covering a garment-side face of the absorbent body;
    buffer regions positioned around the main absorbent region and forming a part of the absorbent body, wherein said buffer regions have a stiffness lower than that of the main absorbent region and include perforations formed in at least one of the upper and lower absorbent sheets, said perforations extending discontinuously along the longitudinal direction thereof;
    side portion reinforcing regions with stiffness larger than the buffer regions, positioned at left and right external sides of the buffer regions and extending in the longitudinal direction; and
    a front reinforcing region and a rear reinforcing region whose bending stiffness in the lateral direction is larger than that of the buffer regions, positioned at front and rear external sides of the buffer regions, connecting continuously, among the side portion reinforcing regions, a left side portion reinforcing region and a right side portion reinforcing region, so that the left side portion and the right side portion do not easily approach one another, and easily recover to their original shape.

* * * * *